(12) United States Patent
Constantineau et al.

(10) Patent No.: US 9,433,757 B2
(45) Date of Patent: Sep. 6, 2016

(54) COMPACT SPRING INSERTER FOR DRUG DELIVERY INFUSION SET

(75) Inventors: Cole Constantineau, Cambridge, MA (US); Ryan Schoonmaker, San Marcos, CA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 390 days.

(21) Appl. No.: 14/002,210

(22) PCT Filed: Feb. 8, 2012

(86) PCT No.: PCT/US2012/000076
§ 371 (c)(1),
(2), (4) Date: Oct. 17, 2013

(87) PCT Pub. No.: WO2012/141759
PCT Pub. Date: Oct. 18, 2012

(65) Prior Publication Data
US 2014/0039458 A1 Feb. 6, 2014

Related U.S. Application Data (60) Provisional application No. 61/448,927, filed on Mar. 3, 2011.

(51) Int. Cl.
*A61M 25/06* (2006.01)
*A61M 5/158* (2006.01)

(52) U.S. Cl.
CPC ......... *A61M 25/0606* (2013.01); *A61M 5/158* (2013.01); *A61M 2005/1581* (2013.01); *A61M 2005/1585* (2013.01); *A61M 2005/1586* (2013.01); *A61M 2005/1587* (2013.01)

(58) Field of Classification Search
CPC ........... A61M 25/0606; A61M 5/158; A61M 2005/1581; A61M 2005/1585–2005/1587
See application file for complete search history.

(56) References Cited

U.S. PATENT DOCUMENTS

| | | |
|---|---|---|
| 6,830,562 B2 | 12/2004 | Mogensen et al. |
| 7,128,727 B2 | 10/2006 | Flaherty et al. |

(Continued)

FOREIGN PATENT DOCUMENTS

| | | |
|---|---|---|
| JP | 2004524926 A1 | 8/2004 |
| JP | 2007216029 A1 | 8/2007 |

(Continued)

*Primary Examiner* — Nathan R Price
*Assistant Examiner* — Melissa A Snyder
(74) *Attorney, Agent, or Firm* — Dickinson Wright PLLC (57) ABSTRACT

An infusion set (101) includes a base (111) and an inserter (121) removably connected to the base (111). A catheter (134) is movable from a first catheter position disposed substantially entirely within the inserter (121) to a second catheter position' in which a free end of the catheter (134) is disposed externally of the base (111). An introducer needle (142) is located within the catheter (134) and is movable with the catheter (134) between a first introducer needle position disposed substantially entirely within the inserter (121) and a second introducer needle position in which a free end of the introducer needle (142) is disposed externally of the base (111). A spring member (171) moves the catheter (134) from the first to the second catheter position and the introducer needle (142) from the first to the second introducer needle position to facilitate insertion of the catheter (134). The spring member (171) is disposed substantially entirely within the base (111) when the catheter (134) is in the second catheter position.

19 Claims, 9 Drawing Sheets

(56) References Cited

U.S. PATENT DOCUMENTS

| | | | |
|---|---|---|---|
| 2004/0158207 A1* | 8/2004 | Hunn | A61M 5/158 604/164.01 |
| 2006/0264890 A1* | 11/2006 | Moberg | A61M 5/1413 604/500 |
| 2006/0282290 A1 | 12/2006 | Flaherty et al. | |
| 2007/0093754 A1 | 4/2007 | Mogensen et al. | |
| 2007/0191772 A1 | 8/2007 | Wojcik | |
| 2008/0154205 A1 | 6/2008 | Wojcik | |
| 2009/0254041 A1* | 10/2009 | Krag | A61M 5/14224 604/180 |

FOREIGN PATENT DOCUMENTS

| | | |
|---|---|---|
| JP | 2010501281 A1 | 1/2010 |
| WO | WO 03/026728 A1 | 4/2003 |
| WO | WO 2006/077262 A1 | 7/2006 |
| WO | 2010037759 | 4/2010 |
| WO | WO2010/037759 A1 * | 4/2010 |
| WO | WO 2010/085338 A1 | 7/2010 |

* cited by examiner

COMPACT SPRING INSERTER FOR DRUG DELIVERY INFUSION SET

CROSS REFERENCE TO RELATED APPLICATION

This application claims the benefit under 35 U.S.C. §119 (e) of U.S. Provisional Patent Application Ser. No. 61/448,927, filed on Mar. 3, 2011, which is hereby incorporated by reference in its entirety.

FIELD OF THE INVENTION

The present invention relates generally to a compact spring inserter for a drug delivery infusion set. More particularly, the present invention relates to an inserter in which a spring member is stored in a base of an infusion set after inserting an introducer needle and a catheter. Still more particularly, the present invention relates to an inserter in which insertion of an introducer needle and catheter at an insertion site is actuated by the rotation of a dial or outer housing.

BACKGROUND OF THE INVENTION

A large number of people suffering from diabetes use some form of daily insulin therapy to maintain close control of their glucose levels. Currently, there are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but is superior from a user perspective. Consequently, the overwhelming majority of patients who have used pumps prefer to remain with pumps for the rest of their lives. Infusion pumps, although more complex than syringes and pens, offer the advantages of continuous infusion of insulin, precision dosing and programmable delivery schedules. This results in closer blood glucose control and an improved feeling of wellness.

The use of an infusion pump requires the use of a disposable component, typically referred to as an infusion set or pump set, which conveys the insulin from a reservoir within the pump into the skin of the user. An infusion set typically consists of a pump connector, a length of tubing, and a hub or base from which an infusion cannula extends. The hub or base has an adhesive that retains the base on the skin surface during use, and may be applied to the skin manually or with the aid of a manual or automatic insertion device. There are many available types of infusion sets, including steel needle infusion sets and soft catheter sets. Soft catheter sets are typically inserted into a patient manually with the aid of a steel needle introducer, which is manually removed from the patient after insertion to leave the soft catheter in place.

One problem associated with manually inserting and retracting the introducer needle is variability in the insertion and retraction force, speed, smoothness and angle. This variability can lead to an increased rate of catheter insertion failure. Further, as noted above, the user typically must remove the introducer needle after inserting the catheter. This exposes the user to accidental needle sticks from handling the removed introducer needle.

In another type of infusion set, a mechanized insertion device is used to forcefully and rapidly insert the introducer needle and catheter, remove the introducer, or both. Often, the insertion device is a separate, stand-alone unit that the user is required to carry and provide. Stand-alone inserters typically require the user to manually load a spring of the inserter, which can result in catheter insertion failure when the spring is not properly loaded.

Accordingly, a need exists for an infusion set and insertion device that facilitates insertion of the catheter, while reducing the number of components a user must carry and substantially preventing accidental needle sticks.

SUMMARY OF THE INVENTION

An object of the present invention is to provide a compact spring inserter for an infusion set, particularly an insulin infusion set.

Another object of the present invention is to provide an infusion set inserter in which a spring member is used to facilitate catheter insertion and is stored in the base of the infusion set after insertion, thereby substantially preventing catheter insertion failure and providing a low profile infusion set.

Another object of the present invention is to provide an infusion set in which a connector of the infusion set connects directly to a catheter hub, thereby reducing the number of components in the fluid path.

In accordance with an exemplary embodiment of the present invention, a drug delivery infusion set houses and stores a spring member that inserts an introducer needle and a catheter at an insertion site. The catheter and introducer needle are inserted from a vertical position of the inserter by rotating an outer housing serving as a dial. The introducer needle is manually removed from the insertion site by disconnecting the inserter from a base. The spring member is stored in the base, allowing the thickness of the infusion set to be reduced. A knob on the inserter withdraws the introducer needle into the housing or dial to shield the introducer needle, thereby substantially preventing accidental introducer needle sticks. Additionally, because the introducer needle is fully retracted from the catheter, the introducer needle is not part of the fluid path, thereby reducing the number of components in the fluid path and substantially preventing leakage and sealing problems.

The foregoing objects are essentially attained by an infusion set including a base and an inserter removably connected to the base. A catheter is movable from a first catheter position disposed substantially entirely within the inserter to a second catheter position in which a free end of the catheter is disposed externally of the base. An introducer needle is located within the catheter and is movable with the catheter between a first introducer needle position disposed substantially entirely within the inserter and a second introducer needle position in which a free end of the introducer needle is disposed externally of the base. A spring member moves the catheter from the first to the second catheter position and the introducer needle from the first to the second introducer needle position to facilitate insertion of the catheter. The spring member is disposed substantially entirely within the base when the catheter is in the second catheter position.

These and other objects are substantially achieved by providing an infusion set having a removable inserter that stores a spring member in a base and withdraws an introducer needle of the infusion set, thereby providing a low profile infusion set. Additionally, accidental introducer needle sticks are substantially prevented by disposing the introducer needle within the removed inserter.

BRIEF DESCRIPTION OF THE DRAWINGS

The above benefits and advantages of the present invention will be more apparent from the following detailed description of an exemplary embodiment of the present invention and from the accompanying drawing figures, in which.

Throughout the drawings, like reference numerals will be understood to refer to like parts, components and structures.

DETAILED DESCRIPTION OF THE EXEMPLARY EMBODIMENTS

The exemplary embodiment of the present invention described below provides a novel means of inserting a soft catheter into the skin. In particular, the exemplary embodiment of the present invention provides an inserter 121 that inserts an introducer needle 142 and a soft catheter 134 into the skin, and then stores a spring member 171 in a base 111 of an infusion set 101, as shown in FIGS. 2, 3, 10 and 14, thereby providing a low profile infusion set.

Figure 2:
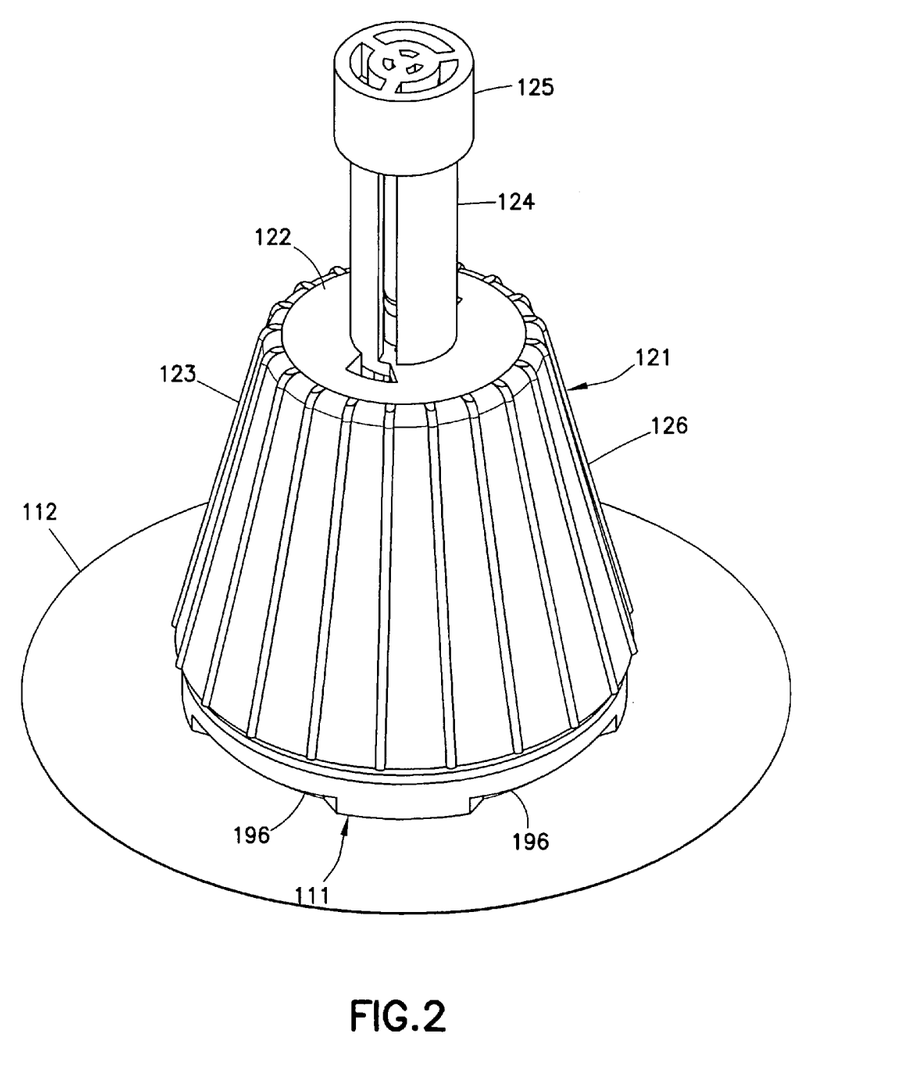
FIG. 2 is a perspective view of an inserter and base in accordance with an exemplary embodiment of the present invention.
Figure 3:
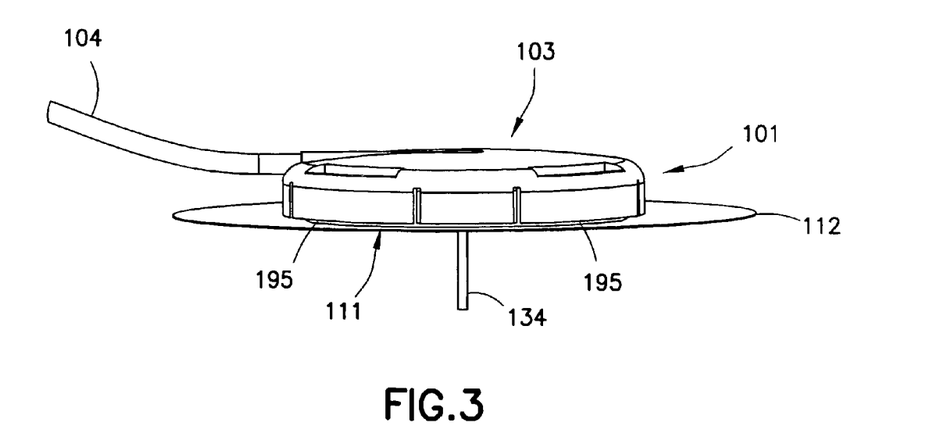
FIG. 3 is a perspective view of an infusion set after removing the inserter of FIG. 2 from the base and connecting the fluid connector of FIG. 1 thereto.
Figure 4:
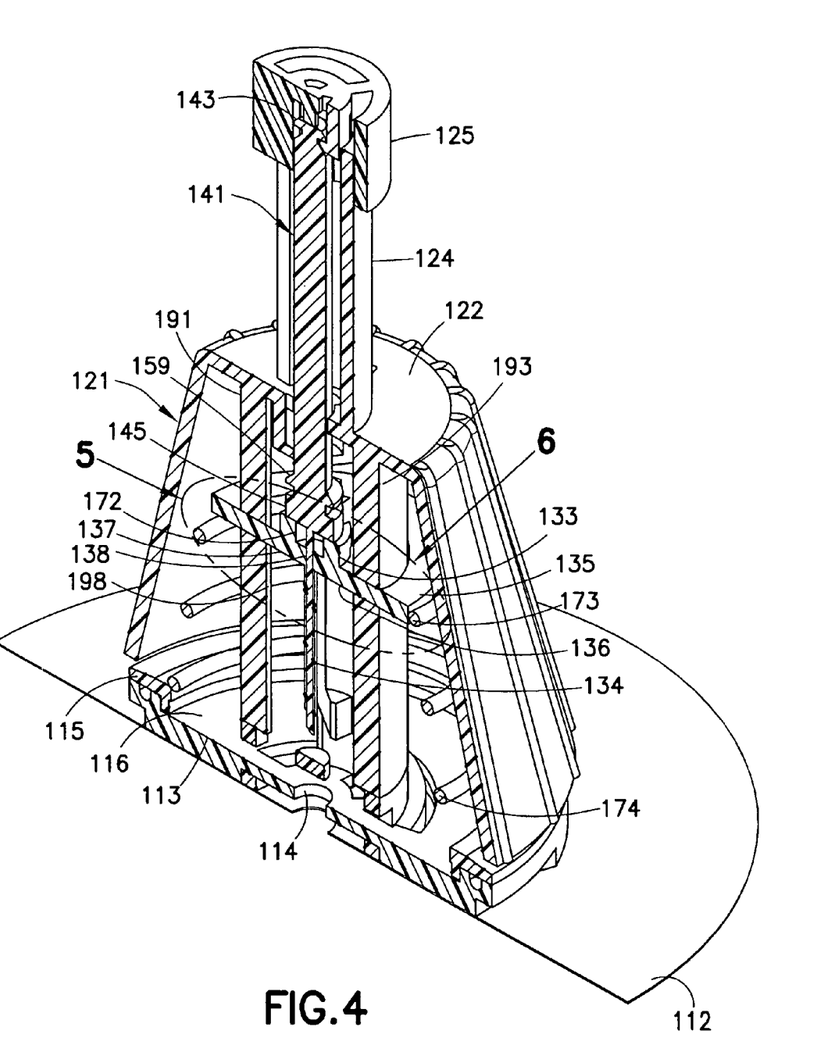
FIG. 4 is a perspective in cross-section of the inserter and base of FIG. 2.
Figure 10:
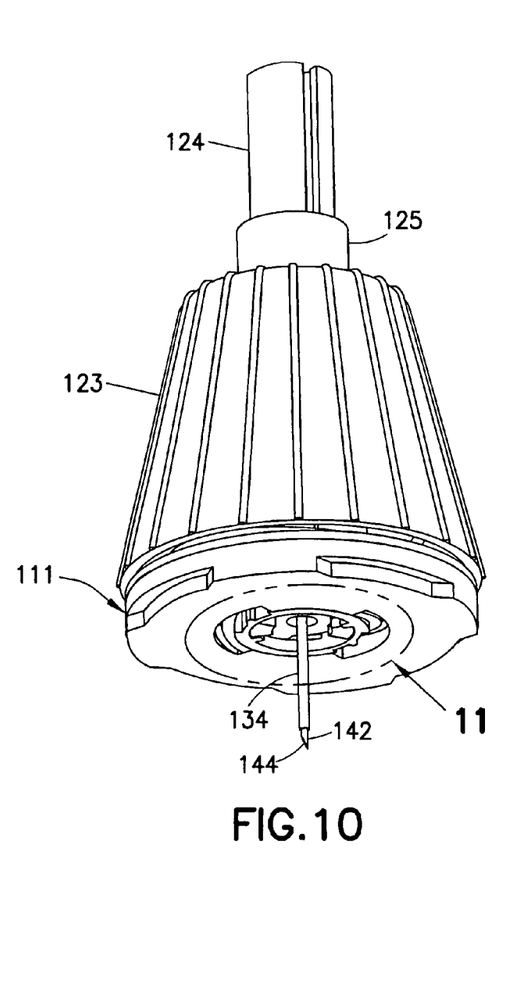
FIG. 10 is a perspective view of the inserter connected to the base with the introducer needle and soft catheter in inserted positions.
Figure 11:
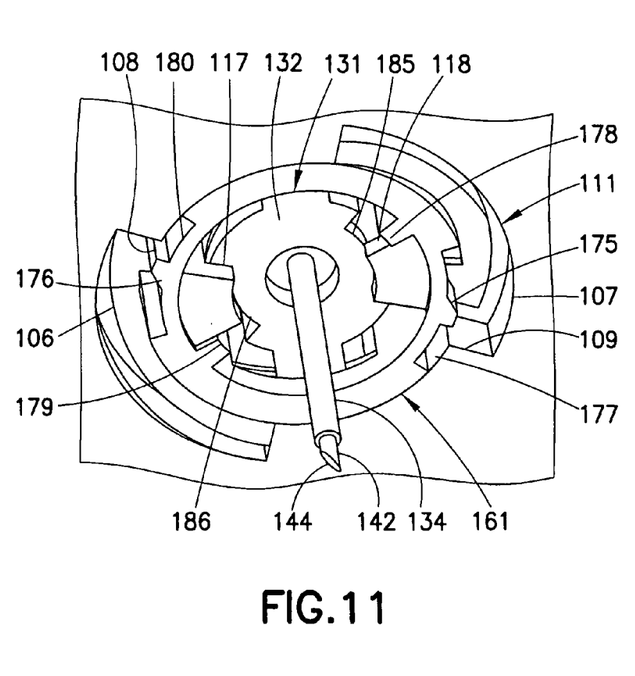
FIG. 11 is an enlarged perspective view of the introducer needle and soft catheter of FIG. 10.

The base 111 of the infusion set is preferably provided with a skin-securing, adhesive layer 112, as shown in FIGS. 2 and 3, to secure the infusion set to the skin surface at the insertion site. The adhesive layer 112 ensures that the base remains at the proper position relative to the skin surface, and that the skin is secured during insertion to further aid introducer needle insertion with a reduced risk of tenting of the skin surface. The base 111 has a planar surface 113 having an opening 114 therein through which the catheter 134 and the introducer needle 142 pass, as shown in FIGS. 4, 10 and 11. A wall 115 extends upwardly from an outer edge of the planar surface 113 such that a cavity 116 is defined by the planar surface and the wall 115, as shown in FIG. 4.

Figure 12:
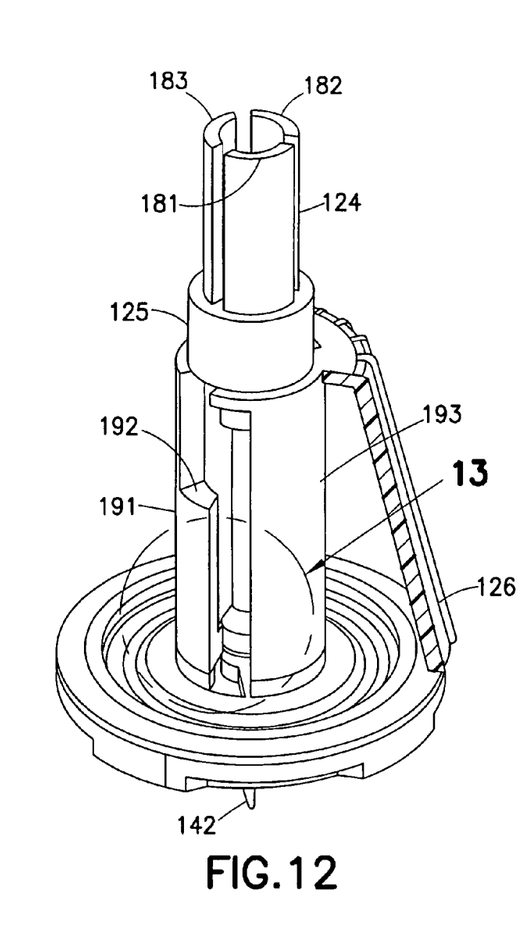
FIG. 12 is a perspective view in partial cross-section showing the disconnection of the inserter from the base.
Figure 13:
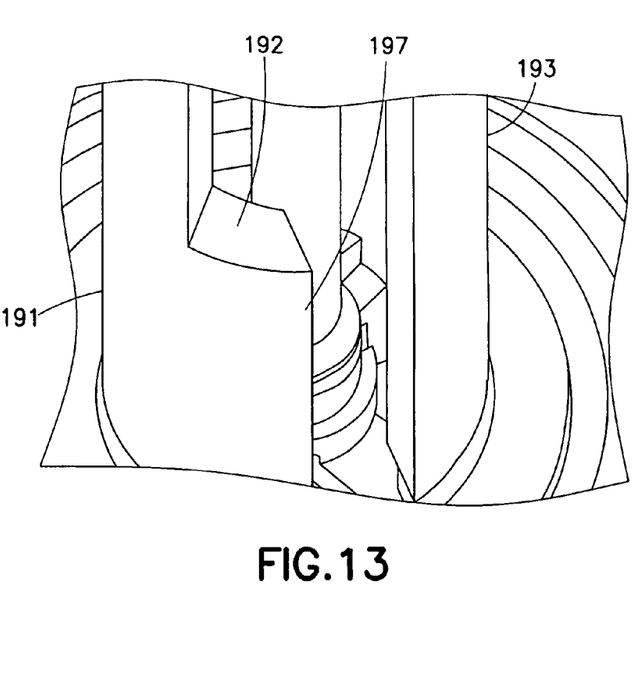
FIG. 13 is an enlarged perspective view of the catheter hub of FIG. 12.
Figure 15:
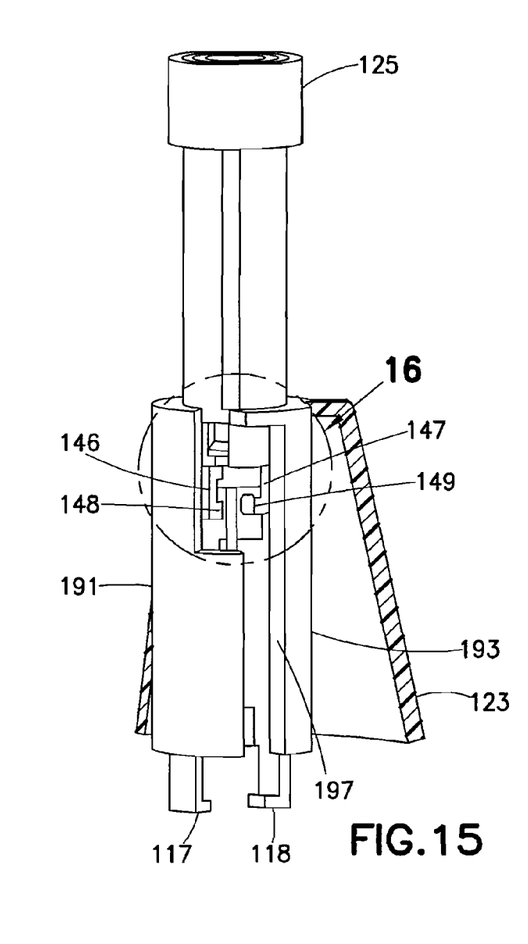
FIG. 15 is a perspective view in partial cross-section of the housing or dial removed from the base.

The inserter 121 includes a housing or dial 123 rotatably connected to the base 111, a dial post 124 extending upwardly from a base 122 of the dial 123, and a knob 125 movably connected to the dial post 124, as shown in FIGS. 2, 4 and 10. The dial 123 has a substantially frustoconical shape, as shown in FIGS. 2 and 4. A wall 126 of the dial 123 extends downwardly and outwardly from the dial base 122 and the dial post 124 extends upwardly from and substantially perpendicularly to the dial base 122. Preferably, the dial post 124 comprises three substantially arcuate members 181, 182 and 183 spaced apart from one another at an upper end thereof, as shown in FIG. 12. First and second arms 191 and 193 extend downwardly from the dial base 122 and are disposed within the dial wall 126. First and second shoulders 192 and 194 are formed on the first and second arms 191 and 193, respectively, as shown in FIG. 6. Slots 197 and 198 are formed between the first and second arms 191 and 193, as shown in FIGS. 4 6. The slots 197 and 198 allow for downward movement of the catheter hub 131. Hooks 117 and 118 connected to the arms 191 and 193, as shown in FIGS. 11 and 15, are received by the base 111. The hooks 117 and 118 engage a lower surface 132 of the base 111, as shown in FIG. 11, to prevent withdrawal of the dial 121 prior to insertion of the catheter 134.

The inserter knob 125 is movable between a first, or up, position, as shown in FIG. 4, and a second, or down, position as shown in FIG. 12. The inserter knob 125 is rigidly fixed to an end of an introducer needle plunger 141. When the knob 125 is in the first position as shown in FIG. 4, the introducer needle 142 is disposed within the dial 123. When the knob 125 is in the second position as shown in FIG. 10, the introducer needle 142 is exposed outside the dial 123.

Figure 5:
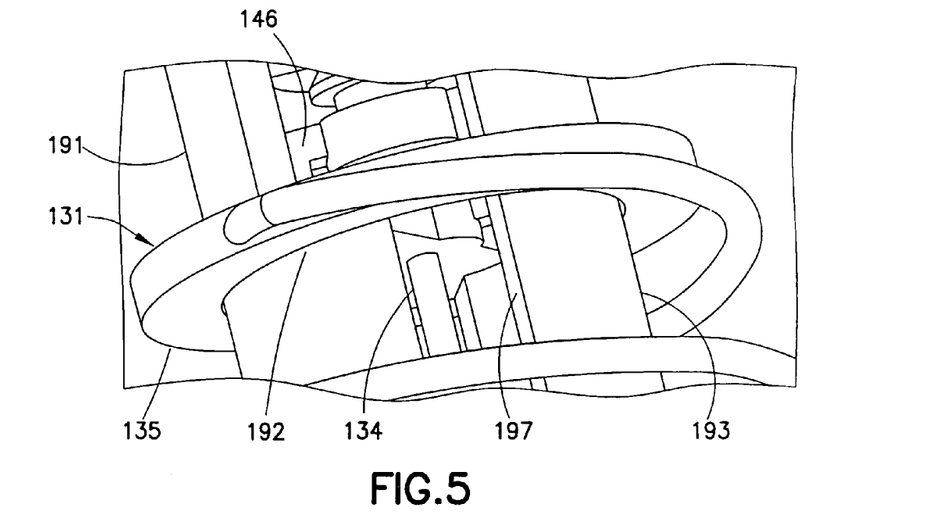
FIG. 5 is an enlarged perspective view of the catheter hub of the inserter of FIG. 4.
Figure 6:
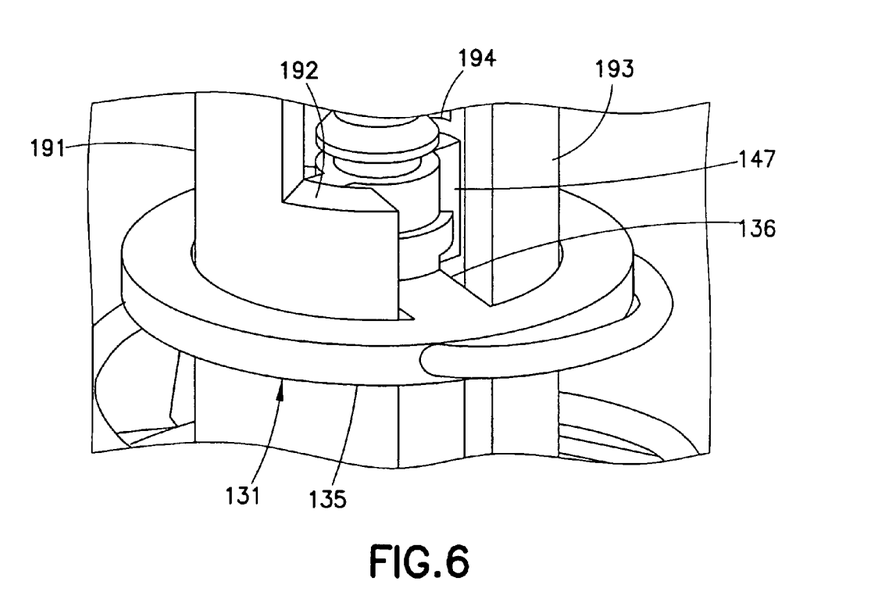
FIG. 6 is an enlarged perspective view of the catheter hub of the inserter of FIG. 4, taken from a different angle.
Figure 14:
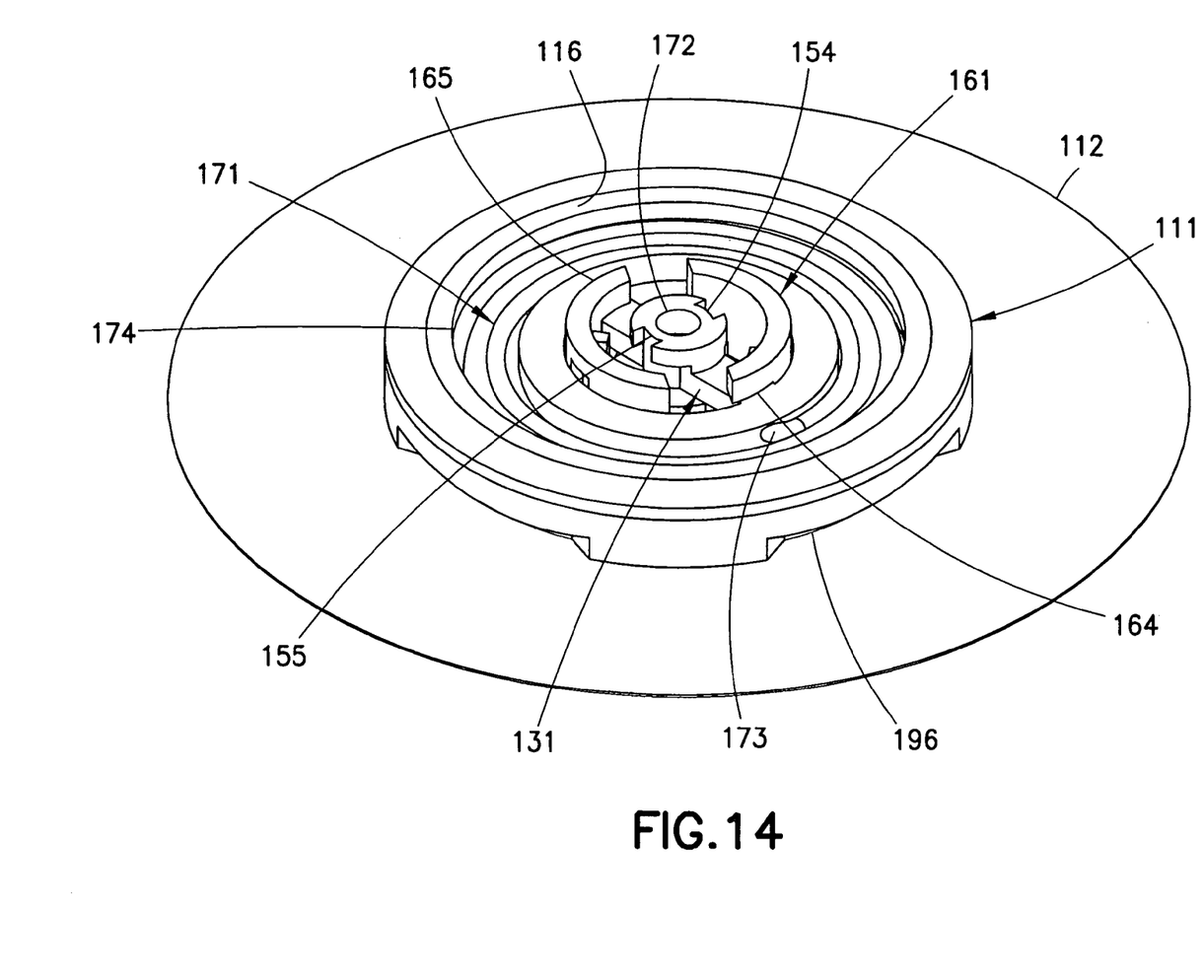
FIG. 14 is a perspective view of the catheter hub locked to the base.

The catheter hub 131 is initially disposed in a first position inside the dial 123, as shown in FIGS. 4 and 5. The catheter hub 131 has an inner ring 133 and an outer ring 135 connected by first and second connecting arms 136 and 137. When the catheter hub 131 is in the first position, the first and second connecting arms 136 and 137 rest on the shoulders 192 and 194 of the arms 191 and 193 of the dial as shown in FIG. 5, thereby preventing downward (toward the base 111) movement of the catheter hub 131. A soft catheter 134 extends downwardly from the inner ring 133 of the catheter hub 131. An opening 138 is disposed in the inner ring 133 of the catheter hub 131 to allow the introducer needle 142 to pass therethrough, as shown in FIG. 4. A septum 172 is disposed inside a recess formed in the inner ring 133 of the catheter hub 131, as shown in FIGS. 4 and 14.

A spring member 171 is disposed within the dial 123, as shown in FIG. 4. A first end 173 of the spring member 171 is connected to the catheter hub 131. A second end 174 of the spring member 171 is connected to the base 111. Preferably, the spring member 171 is a volute extension spring such that each subsequent coil of the spring member from the first end 173 to the second end 174 has a larger diameter. A volute spring is a compression spring that is typically substantially cone-shaped. When the volute spring is under compression the coils are not forced against each other, but instead nest within each other, thus permitting longer travel and increased compactness in the compressed configuration. As shown in FIG. 4, the spring member 171 is initially in tension with the catheter hub 131 resting on the shoulders 192 and 194 of the arms 191 and 193 to prevent downward movement of the catheter hub 131. When the spring member 171 is released, the spring member 171 collapses, thereby pulling the catheter 134 and the introducer needle 142 into the insertion site. As shown in FIG. 14, the spring member 171 collapses upon itself forming a substantially disc-shaped member having a low profile that is substantially entirely received within the cavity 116 in the base 111.

The introducer needle plunger 141 has a first end 143 and a second end 145, as shown in FIG. 4. The first end 143 is rigidly connected to the knob 125, such that the knob moves with the plunger 141. The introducer needle 142 is rigidly connected to the second end 145 such that the introducer moves with movement of the plunger 141. The plunger 141 moves within the dial post 124 for movement external of the dial 123 and within the arms 191 and 193 for movement within the dial 123. The plunger 141 is movable from a first position shown in FIG. 4, to a second position shown in FIG. 12 and back to the first position. First and second plunger arms 146 and 147 have hooks 148 and 149, as shown in FIGS. 5, 6, 15 and 16, that engage a lower surface 132 of the catheter hub 131. Recesses 185 and 186 in the outer circumference of the catheter hub 131 allow for the plunger 141 to be disengaged from the catheter hub after the catheter 134 has been inserted.

Figures 7, 8, 9:
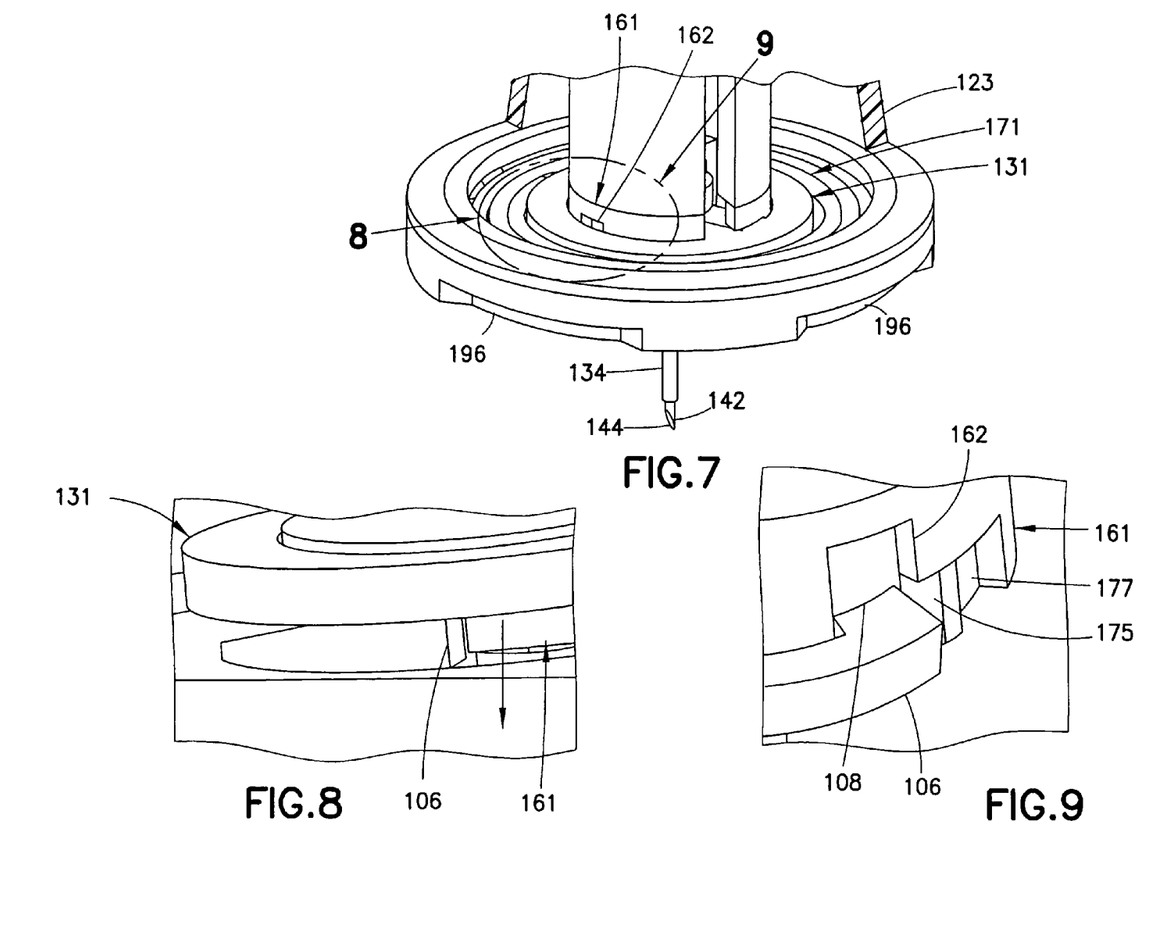
FIG. 7 is a partial perspective view of the catheter hub of the inserter received by the base of FIG. 4.
FIG. 8 is an enlarged perspective view of the catheter hub engaging a base snap.
FIG. 9 is an enlarged perspective view of the base snap disengaging from the housing or dial.

The introducer needle 142 passes through the septum 172 and through the catheter 134 such that an end 144 of the introducer needle is exposed outside of the catheter 134, as shown in FIGS. 7, 10 and 11, when the catheter hub 131 is in the second position. The end 144 of the introducer needle end 142 is sharp to facilitate piercing the skin at a desired catheter insertion point. When the plunger 141 is in the first position (FIG. 4), the introducer needle 142 is not exposed outside the dial 123. When the plunger 141 is in the second position (FIG. 12), the introducer needle 142 is exposed externally of the dial 123 and the base 111 such that the introducer needle can pierce the skin at the desired catheter insertion point.

A locking member 161 is rotationally disposed in the base 111, as shown in FIG. 4. Snap arms 106 and 107 connected to the base 111, as shown in FIGS. 8, 9 and 11, have hooks 108 and 109 that are received in recesses 162 of the locking member 161, as shown in FIG. 9, to prevent rotation of the locking member 161 with respect to the base 111 prior to insertion of the catheter 134. The snap arms 106 and 107 are moved downwardly by the catheter hub 131 during insertion such that the hooks 108 and 109 are moved out of the recesses 162, as shown in FIGS. 8 and 9, thereby allowing the locking member 161 to rotate. The locking member 161 has overhangs 164 and 165 that are rotated after insertion of the catheter 134 that rotate over the catheter hub 131, as shown in FIG. 14, thereby locking the catheter hub 131 to the base 111.

Figure 1:
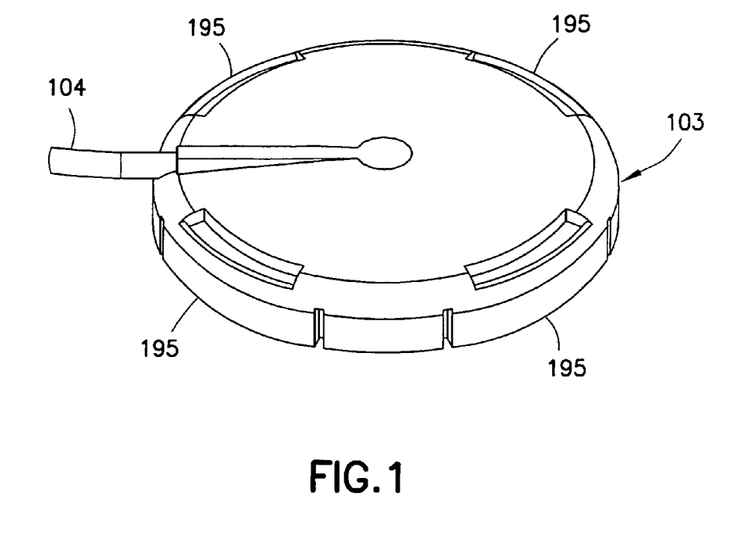
FIG. 1 is a perspective view of a fluid connector of an infusion set in accordance with an exemplary embodiment of the present invention.

A connector 103 has a plurality of flexible arms 195 adapted to engage the corresponding recesses 196 in the outer surface of the base 111, as shown in FIGS. 1-3. Tubing 104 extends from the connector 103 and is adapted to connect to a pump. The tubing 104 is connected to a penetrating member, or sharp (not shown), extending downwardly from the connector 103, and a fluid path is formed therebetween. The penetrating member is adapted to penetrate the septum 172 when the connector 103 is connected to the base 111, as shown in FIG. 3, thereby creating a fluid path between the tubing 104 and the catheter 134.

Assembly and Operation

FIG. 2 is a perspective view of the base 111 and inserter 121 as received by the user. The hooks 117 and 118 of the inserter 121 engage the lower surface 132 of the base 111, as shown in FIG. 11, thereby preventing the inserter 121 from being removed from the base. The knob 125 is in the first, or up, position, as shown in FIG. 2, such that the catheter 134 and the introducer needle 142 are substantially entirely disposed within the dial body 123, as shown in FIG. 2, thereby substantially preventing accidental introducer needle sticks. The connector 103 (FIG. 1) is not yet connected to the base 111 because the catheter 134 has not yet been inserted. The spring member 171 is in tension, as shown in FIG. 4.

Before inserting the catheter 134, a backing (not shown) is removed to expose an adhesive layer 112 so that the base 111 can be adhered to the skin surface at the desired catheter insertion site. Prior to catheter insertion, the catheter hub 131 rests on the shoulders 192 and 194 of the dial arms 191 and 193, thereby preventing downward movement of the catheter hub 131. To insert the catheter 173, the dial 123 is rotated clockwise. The adhesive layer 112 provides a counter-rotation force to resist movement of the base 111 when the dial 123 is rotated. The rotation of the dial 123 causes the dial arms 191 and 193 to rotate, thereby moving the shoulders 192 and 194 of the dial arms 191 and 193 out of engagement with the catheter hub 131, as shown in FIG. 6. The catheter hub arms 136 and 137 are now aligned with the slots 197 and 198 between the base arms 191 and 193, such that the stored energy in the stretched spring member 171 pulls the catheter hub 131 downwardly (i.e., toward the base 111). The slots 197 and 198 guide the catheter hub 131 through its downward movement to the base 111. The catheter 134 is rigidly connected to the catheter hub 131 so that the catheter 134 is pulled downwardly with the catheter hub 131. The plunger hooks 148 and 149 engage the catheter hub 131 so that the introducer needle 142, which is rigidly connected to the plunger 141, is also pulled downwardly with the catheter hub 131. Additionally, the knob 125, which is connected to the first end 143 of the plunger 141, is pulled downwardly along the dial post 124, as shown in FIG. 10. The movement of the knob 125 to the second, or down, position indicates to the user that the introducer needle 142 and catheter 134 have been inserted.

The hooks 108 and 109 of the snap arms 106 and 107 of the base 111 are received in recesses 162 in the locking member 161 prior to insertion of the introducer needle 142 and catheter 134, thereby preventing movement of the locking member 161. Tabs 178 and 179 extending radially inwardly from the locking member 161 engage hooks 117 and 118 of the dial 123, as shown in FIG. 11, thereby preventing further rotation, and hence withdrawal, of the dial prior to the catheter 134 and introducer needle 142 being inserted. When the spring member 171 pulls the catheter hub 131 into the cavity 116 in the base 111, the catheter hub 131 engages the base snap arms 106 and 107 and pushes them downwardly, as shown in FIGS. 8 and 9. The downward movement of the base snap arms 106 and 107 moves the hooks 108 and 109 out of the recesses 162 in the locking member 161, thereby allowing the locking member 161 and dial 123 to be rotated. The catheter 134 and introducer needle 142 have now been inserted in the insertion site, as shown in FIGS. 10 and 11.

The dial 123 can now be further rotated clockwise. Rotation of the dial hooks 117 and 118 causes rotation of the locking member tabs 178 and 179. The rotation of the locking member 161 causes the base snap arms 106 and 107 to slide along ramps 175 and 176 on the outer surface of the locking member and into locking recesses 177 and 180, as shown in FIGS. 9 and 11. The rotation of the locking member 161 also causes the locking member overhangs 164 and 165 to rotate over the catheter hub 131, as shown in FIG. 12, thereby locking the catheter hub 131 to the base 111.

The rotation of the dial 123 moves the hooks 117 and 118 to engage recesses 185 and 186 in the base 111, as shown in FIG. 11. The plunger hooks 148 and 149 are also rotated by rotation of the dial 123 to engage recesses 154 and 155 in the catheter hub 131. Accordingly, the inserter 121, including the dial 123 and plunger 141, can be removed from the base 111, as shown in FIGS. 14 and 15. The spring member 171, catheter hub 131 and locking member 161 remain in the base 111, as shown in FIG. 14, such that the catheter 134 remains inserted in the insertion site and the introducer needle 142 is withdrawn from the insertion site.

The septum 172 in the catheter hub 131 is now exposed, as shown in FIG. 14. The soft catheter 134 remains inserted below the skin and in a substantially vertical position after the dial 123 has been rotated and removed from the base 111, i.e., the soft catheter 134 does not bend with the rotational movement of the dial 123. Accordingly, piercing the septum 172 provides a direct fluid path to the soft catheter 134 as the introducer needle 142 is not part of the fluid path.

A penetrating member, or sharp (not shown), on the fluid connector 103 can now penetrate the septum 172, thereby creating a fluid connection between the catheter 134 and the tubing 104. The user can prime the connector 103 prior to connecting it to the infusion set base 111. Flexible arms 195 of the connector 103 engage recesses 196 in the base 111 to removably connect the connector 103 to the base 111. The infusion set 101, as shown in FIGS. 1 and 3, is now ready to begin infusing insulin. The connector 103 can be removed and reattached to the infusion set base 111 at any time by disengaging and connecting the flexible arms 195 with the base recesses 196. The septum 172 provides a sterility barrier when the penetrating member is removed therefrom, and the fluid connection is reestablished by reinserting the penetrating member through the septum 172 located in the catheter hub 131, which is secured by the locking member 161 in the base 111.

Figure 16:
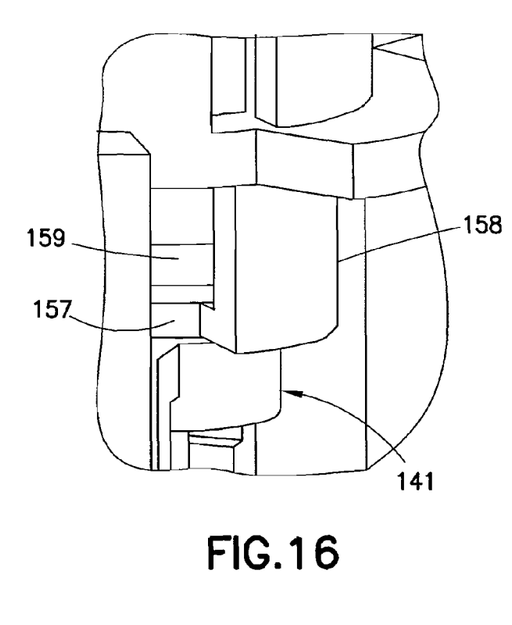
FIG. 16 is an enlarged perspective view of the introducer needle withdrawn into the housing or dial.

The knob 125 of the removed inserter 121 is moved back to the first, or up position, as shown in FIG. 15, thereby lifting the plunger 141 and withdrawing the introducer needle 141 to a protected position within the housing or dial 123. As shown in FIGS. 4, 15 and 16, the knob 125 is lifted until the recess 157 in the plunger 141 engages the hook 158 of the dial 123. The dial hook 158 engages the plunger recess 157, thereby preventing downward movement of the plunger 141 and substantially preventing accidental introducer needle sticks.

The exemplary embodiment described above can be adapted for use with either subcutaneous or intradermal injections. In addition, a different method of maintaining the fluid connection is possible other than through the penetrating member 197 and septum 172. For example, a sliding gasket seal can be used. Alternative methods can be used to insert the catheter and introducer. For example, an angled needle in contact with the skin and driven horizontally can be used to enter the subcutaneous or intradermal layers of the skin. Alternative methods of connecting the connector to the base can be used to facilitate connecting and disconnecting of the connector. Preferably, a ramped surface 159, as shown in FIGS. 4 and 16, is provided on the plunger 141 above the recess 157 to facilitate pulling the plunger 141 upwardly to engage the dial hook 158. Alternatively, the introducer needle 142 can be withdrawn from the insertion site and stored in the base 111 after inserting the catheter 134 instead of being withdrawn from the base with the inserter 121.

Although the exemplary embodiment described above is an infusion set, it will be apparent to those of ordinary skill in the art that the principles of the present invention are also applicable to patch pumps (self-contained infusion devices with integral reservoirs and pumping mechanisms) and other types of medical infusion and injection devices.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the appended claims and their equivalents.

The invention claimed is:

1. An infusion set, comprising:
   a base;
   an inserter removably connected to said base and rotatable to initiate operation of said infusion set;
   a catheter movable from a first catheter position disposed substantially entirely within said inserter to a second catheter position upon rotation of said inserter in which a free end of said catheter is disposed externally of said base;
   an introducer needle located within said catheter and movable with said catheter between a first introducer needle position disposed substantially entirely within said inserter and a second introducer needle position upon rotation of said inserter in which a free end of said introducer needle is disposed externally of said base; and
   a spring member for moving said catheter from said first to said second catheter position and said introducer needle from said first to said second introducer needle position to facilitate insertion of said catheter, said spring member being disposed substantially entirely within said base when said catheter is in said second catheter position.

2. The infusion set in accordance with claim 1, wherein said spring member is a volute spring.

3. The infusion set in accordance with claim 1, wherein said spring member is activated by rotating said inserter relative to said base.

4. The infusion set in accordance with claim 1, wherein said inserter is removable from said base by rotating said inserter relative to said base when said catheter is in said second position.

5. The infusion set in accordance with claim 4, wherein said introducer needle is removable from said base with said inserter, said introducer needle being substantially entirely disposed within said removed inserter.

6. The infusion set in accordance with claim 1, wherein said introducer needle and said catheter enter a skin surface at a substantially perpendicular angle to the skin surface.

7. The infusion set in accordance with claim 1, wherein a septum disposed in said base is exposed by removal of said inserter to receive a fluid connector.

8. The infusion set in accordance with claim 4, wherein said catheter is locked to said base when said inserter is rotated for removal from said base.

9. An infusion set, comprising:
a base;
an inserter removably connected to said base and rotatable to initiate operation of said infusion set;
a catheter hub movable from a first catheter hub position to a second catheter hub position;
a catheter connected to said catheter hub and movable from a first catheter position to a second catheter position upon rotation of said inserter, said catheter being disposed substantially entirely within said inserter when said catheter hub is in said first catheter hub position and said catheter is in said first catheter position and said catheter having a free disposed externally of said base when said catheter hub is in said second catheter hub position and said catheter is in said second catheter position;
an introducer needle located within said catheter and movable with said catheter and said catheter hub from a first introducer needle position to a second introducer needle position upon rotation of said inserter, said introducer needle being disposed substantially entirely within said inserter when said introducer needle is in said first introducer needle position and said introducer needle having a free end disposed externally of said base when said introducer needle is in said second introducer needle position; and
a spring member for moving said catheter hub, said catheter and said introducer needle, wherein prior to activating said spring member, said catheter hub, said catheter and said introducer needle are in said first catheter hub position, said first catheter position and said first introducer needle position, respectively, and when said spring member is activated, said catheter hub is moved to said second catheter hub position, said catheter is moved to said second catheter position and said introducer needle is moved to said second introducer needle position and then retracted to said first introducer hub position, said spring member being disposed entirely within said base when said catheter hub is in said second catheter hub position.

10. The infusion set in accordance with claim 9, wherein said catheter hub engages an inner shoulder of said inserter to retain said catheter hub in said first catheter hub position.

11. The infusion set in accordance with claim 10, wherein rotation of said inserter disengages said inner shoulder of said inserter from said catheter hub such that said spring member moves said catheter hub to said second catheter hub position.

12. An infusion set, comprising:
a base;
an inserter removably connected to said base;
a catheter hub movable from a first catheter hub position to a second catheter hub position;
a catheter connected to said catheter hub and movable from a first catheter position to a second catheter position, said catheter being disposed substantially entirely within said inserter when said catheter hub is in said first catheter hub position and said catheter is in said first catheter position and said catheter having a free disposed externally of said base when said catheter hub is in said second catheter hub position and said catheter is in said second catheter position;
an introducer needle located within said catheter and movable with said catheter and said catheter hub from a first introducer needle position to a second introducer needle position, said introducer needle being disposed substantially entirely within said inserter when said introducer needle is in said first introducer needle position and said introducer needle having a free end disposed externally of said base when said introducer needle is in said second introducer needle position; and
a spring member for moving said catheter hub, said catheter and said introducer needle, wherein prior to activating said spring member, said catheter hub, said catheter and said introducer needle are in said first catheter hub position, said first catheter position and said first introducer needle position, respectively, and when said spring member is activated, said catheter hub is moved to said second catheter hub position, said catheter is moved to said second catheter position and said introducer needle is moved to said second introducer needle position and then retracted to said first introducer hub position, said spring member being disposed entirely within said base when said catheter hub is in said second catheter hub position, wherein
said catheter hub engages an inner shoulder of said inserter to retain said catheter hub in said first catheter hub position,
rotation of said inserter disengages said inner shoulder of said inserter from said catheter hub such that said spring member moves said catheter hub to said second catheter hub position, and
rotation of said inserter when said catheter hub is in said second catheter hub position moves a locking member into engagement with said catheter hub to lock said catheter hub to said base.

13. The infusion set in accordance with claim 11, wherein rotation of said inserter when said catheter hub is in said second catheter hub position disengages said inserter from said base to remove said inserter from said base.

14. The infusion set in accordance with claim 13, wherein said introducer needle is removed from said base with said inserter, said introducer needle being substantially entirely disposed within said removed inserter.

15. The infusion set in accordance with claim 9, wherein
a plunger is removably connected to said catheter hub; and
said introducer needle is rigidly connected to said plunger.

16. An infusion set, comprising:
a base;
an inserter removably connected to said base;
a catheter hub movable from a first catheter hub position to a second catheter hub position;
a catheter connected to said catheter hub and movable from a first catheter position to a second catheter position, said catheter being disposed substantially entirely within said inserter when said catheter hub is in said first catheter hub position and said catheter is in said first catheter position and said catheter having a free disposed externally of said base when said catheter hub is in said second catheter hub position and said catheter is in said second catheter position;
an introducer needle located within said catheter and movable with said catheter and said catheter hub from a first introducer needle position to a second introducer needle position, said introducer needle being disposed substantially entirely within said inserter when said introducer needle is in said first introducer needle position and said introducer needle having a free end disposed externally of said base when said introducer needle is in said second introducer needle position; and a spring member for moving said catheter hub, said catheter and said introducer needle, wherein prior to activating said spring member, said catheter hub, said catheter and said introducer needle are in said first catheter hub position, said first catheter position and said first introducer needle position, respectively, and when said spring member is activated, said catheter hub is moved to said second catheter hub position, said catheter is moved to said second catheter position and said introducer needle is moved to said second introducer needle position and then retracted to said first introducer hub position, said spring member being disposed entirely within said base when said catheter hub is in said second catheter hub position, wherein a first end of said spring member is connected to said catheter hub and a second end of said spring member is connected to said base.

17. A method of inserting a catheter of an infusion set, comprising the steps of disposing an infusion set base and an inserter on a skin surface at an injection site while said infusion set base is coupled to said inserter;

rotating said inserter to activate a spring member;

inserting an introducer needle and the catheter through the skin surface upon activation of the spring member of the inserter;

removing the inserter from the infusion set base; and storing the spring member in the infusion set base.

18. The method of inserting a catheter of an infusion set in accordance with claim 17, wherein removing the inserter removes the introducer needle with the inserter.

19. The method of inserting a catheter of an infusion set in accordance with claim 17, wherein rotating the inserter after inserting the introducer needle and the catheter removes the inserter from the infusion set base and exposes a septum of the infusion set base to receive a fluid connector.

* * * * *